United States Patent
Weissenfluh et al.

[11] Patent Number: 5,951,801
[45] Date of Patent: Sep. 14, 1999

[54] METHOD FOR JOINING A METAL FOIL WITH A FOIL OF A SYNTHETIC MATERIAL

[75] Inventors: Beat A. v. Weissenfluh, Gentilino; Beat Kilcher, Bosco Luganese, both of Switzerland

[73] Assignee: Hawe Neos Dental DR. H. v. Weissenfluh AG, Bioggio, Switzerland

[21] Appl. No.: 08/848,234

[22] Filed: Apr. 29, 1997

[30] Foreign Application Priority Data

Apr. 29, 1996 [CH] Switzerland ............... 1076/96

[51] Int. Cl.$^6$ ................................. B32B 31/08
[52] U.S. Cl. ............ 156/164; 156/269; 156/272.6; 156/275.7; 156/324; 156/544; 433/39
[58] Field of Search ................. 156/164, 229, 156/269, 272.6, 275.7, 324, 549, 544, 546, 275.5; 433/39

[56] References Cited

U.S. PATENT DOCUMENTS

| | | | |
|---|---|---|---|
| 1,410,879 | 3/1922 | Bither | 156/324 |
| 3,660,190 | 5/1972 | Stroszynski | 156/272.6 |
| 3,776,798 | 12/1973 | Milano | 156/269 |
| 4,119,479 | 10/1978 | Williams et al. | 156/275.7 |
| 4,496,417 | 1/1985 | Haake et al. | 156/361 |
| 4,523,909 | 6/1985 | Lazarus | 433/39 |
| 5,330,353 | 7/1994 | Wavrin | 433/39 |
| 5,393,818 | 2/1995 | Masse et al. | 524/270 |

FOREIGN PATENT DOCUMENTS

| | | |
|---|---|---|
| 0124847 | 11/1984 | European Pat. Off. |
| 0180901 | 5/1986 | European Pat. Off. |
| 2553029 | 10/1983 | France |
| 2575450 | 12/1985 | France |

OTHER PUBLICATIONS

Database WPI, Section Ch, Week 8035, Derwent Publications Ltd., London, GB; Class A32, AN80–61592C XP002021462 & JP 55 095 565 A (Matsushita Elec Works), Jul. 20, 1980, Zusammenfassung.

*Primary Examiner*—Michael W. Ball
*Assistant Examiner*—Michael A. Tolin
*Attorney, Agent, or Firm*—Foley & Lardner

[57] ABSTRACT

The method for joining a metal foil with a synthetic material foil comprises unwinding both materials from a supply roll each, and subjecting the synthetics foil, prior to the application of an adhesive, to a corona discharge on a narrow border region. The metal foil and the synthetic material foil are then pressed together and irradiated by ultraviolet radiation causing polymerization of the adhesive. The composite foil material thus obtained is transferred to a further processing station. There the dental matrix can be punched out of such a composite sheet material, having a high tensile strength, whose metal portion can easily be inserted between two adjacent teeth whereas the transparent synthetic material part allows light curing of the dental filling material.

19 Claims, 2 Drawing Sheets

METHOD FOR JOINING A METAL FOIL WITH A FOIL OF A SYNTHETIC MATERIAL

FIELD OF THE INVENTION

The present invention is related to a method of joining a metal foil with a foil of a synthetic material by adhesive bonding and in particular to a method of manufacturing a dental matrix by joining a metal foil with a foil of synthetic material and punching out the shape of the matrix.

BACKGROUND OF THE INVENTION

Such a composite matrix has been disclosed in the U.S. Pat. No. 5,330,353, and clinical tests have shown that the metallic part of the matrix makes easier the introduction of the matrix between two teeth, whereas the synthetics part is necessary for the exposure of teeth fillings of polymerizable synthetic material to light. In the mentioned U.S. patent, relatively few indications can be found referring to the manufacture of such a composite matrix; it is only said that the metal foil is joined to the synthetics foil by microetching and heat sealing.

SUMMARY OF THE INVENTION

In view of the desired low thickness of the foils, on one hand, and the relatively high tensile strength of the composite foil required by the matrix tension device to be used, on the other hand, it is the first and major object of the present invention to provide a process for establishing a connection or joint between a metal foil and a foil of a synthetic material which allows the joining of very thin foils and which yields a high tensile strength. Another object of the invention is to provide such a method which allows the combining of metal foil with thermoplastic foils by adhesive bonding. Still a further object of the present invention is to provide a new and useful dental matrix having reduced thickness and improved tensile strength.

These objects are met by the method of the invention which comprises unwinding the foils from a supply roll each and subjecting the synthetic material foil, prior to the application of a light curing adhesive, to a corona discharge on at least a small border region of the foil, whereupon both foils are then pressed together and irradiated by light, in particular ultraviolet light, in order to cause polymerization of the adhesive. With the method for producing dental matrices the composite foil thus obtained is transferred by a transportation device to a processing station for punching out the matrices.

Preferably, each foil is tensioned separately after unwinding from the supply roll by using a tension regulator. The stretch ratio for both foils or foils should be essentially about the same; this requires a tensioning of the metal foil for more than 20 times that of the synthetics foil. Preferably too, the two foils or foils are offset to such an extent that an overlapping width for cementing of about 2 to 4 mm is obtained. The metal foil is typically a steel foil having a thickness of about 0.02 to 0.06 mm, advantageously of about 0.03 to 0.04 mm, and the synthetics foil is a thermoplastic polyester foil, for example a foil of polyethylene terephthalate.

The invention shall now further be explained by means of an example and with reference to the drawing.

DETAILED DESCRIPTION OF THE INVENTION

Figure 1:
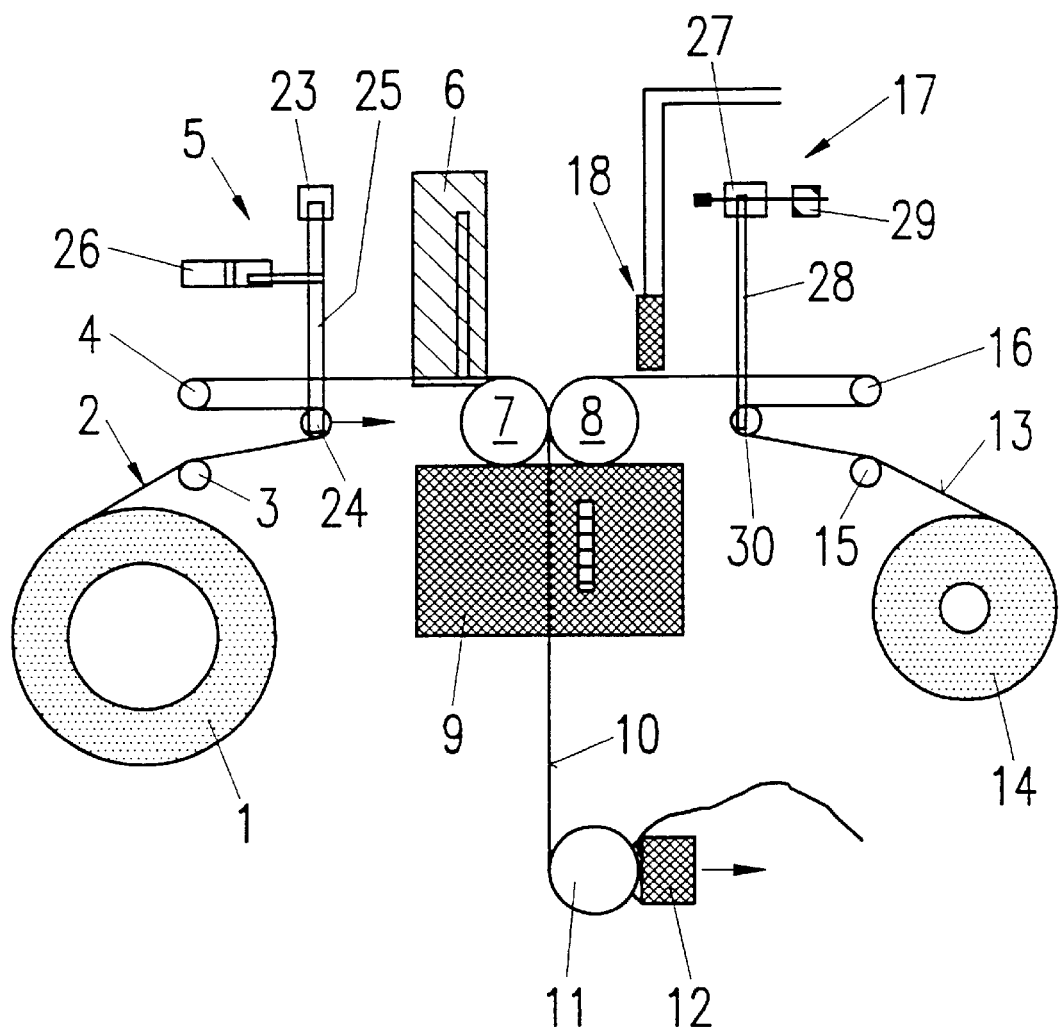
FIG. 1 schematically shows an apparatus for carrying out the method of this invention.

FIG. 1 shows, from the left to the right, the supply roll 1 for the metal foil 2 which is guided over deflector rollers 3 and 4 to a tensioning and control device 5 which is abbreviated in the following as tension regulator, and then to a metering unit 6 where an adhesive, capable of being cured by light, in particular ultraviolet (UV) light, is applied. The adhesive is applied to a narrow edge portion of the foil within an overlapping region of about 2 to 4 mm, preferably about 3 mm. The foil is then transported to the coacting pressure rollers 7 and 8 where the metal foil is pressed together with the synthetics foil.

The synthetic material foil 13 is unwound from the supply roll 14 and is then fed to the deflector rollers 15 and 16 and the required tension is correctly adjusted by a second tension regulator 17. Shortly before arriving at the pressure rollers 7 and 8, at least the edge portion of the synthetics foil to be cemented is passed through a corona discharge station 18 in order to achieve a better wet-tability of the synthetic material by raising its surface energy. This treatment results in that, on one hand, the connection between metal and synthetics is improved and, on the other hand, only a relatively small overlapping suffices for obtaining the required tensile strength.

The adhesive bearing metal foil and the corona treated synthetics foil are combined in the gap between the pressure rollers 7 and 8. The resulting composite foil is then passed through the polymerizing station 9 in which the cemented region is irradiated with UV light. Then, the composite foil 10 is transported to a roller 11 equipped with a pressure device 12 and further to a punching tool (not shown) where ready-for-use matrices are manufactured.

Figure 2:
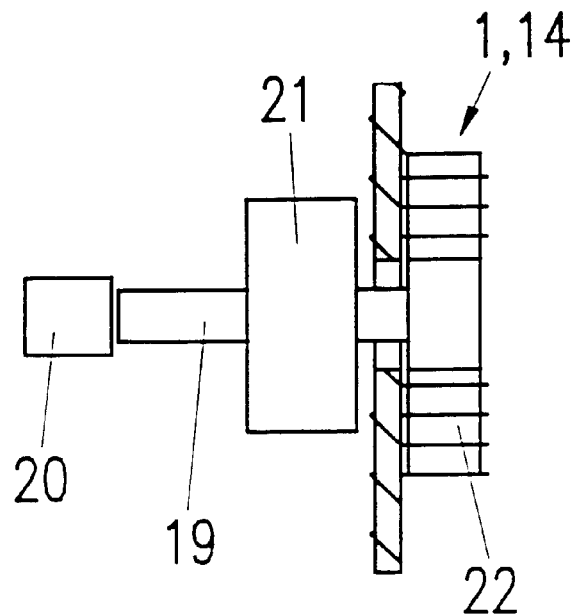
FIG. 2 shows an enlarged portion of the apparatus according to FIG. 1.

The rollers 1 and 14 are positively driven. In the embodiment shown in FIG. 2, the shaft 19 is driven by a motor 20, and a reduction gear 21 is connected to the shaft which has, for example, a reduction ratio of 1:40 and which acts on the spool 22.

The two tension regulators 5 and 17 have in principle the same objective but the solution is respectively different since different forces are required to act on the metal foil and the synthetics foil. Thus, the tension regulator 5 contains a measuring gauge 23 fastened to a lever 25 which is connected to a deflector roller 24. A pneumatically driven cylinder 26 acts on the lever 25 in order to generate a tension of, e.g., 50 N at the deflector roller 24.

The measuring gauge 27 of the tension regulator 17 is articulated to a lever 28 on which acts also a force consisting for example of a mass 29 in order to exert a tension force on the deflector roller 30. This tension force should of course be smaller for tensioning the synthetics foil as the metal foil and may be, for example, about 2 N. It is important that the elongation of both foils will be about the same for avoiding the curling of the composite foil like an angel's hair after polymerization of the adhesive. The station 18 for generating a corona discharge is known per se and needs not be described in more detail.

It becomes clear from the description that the two supply rolls 1 and 14 and the foils 2 and 13 are offset to each other in such a manner that there is only a relatively narrow overlapping of 2 to 4 mm, preferably 3 mm. Of course, a differently large overlapping may be selected as an optimum depending on the adhesive and/or foil materials used. The roller 11 is also driven by a motor (not shown) whereas the pressure device 12 comprises appropriate counter-rollers (not shown). The following punching device is not represented in the drawing and may be considered as known per se.

Figure 3:
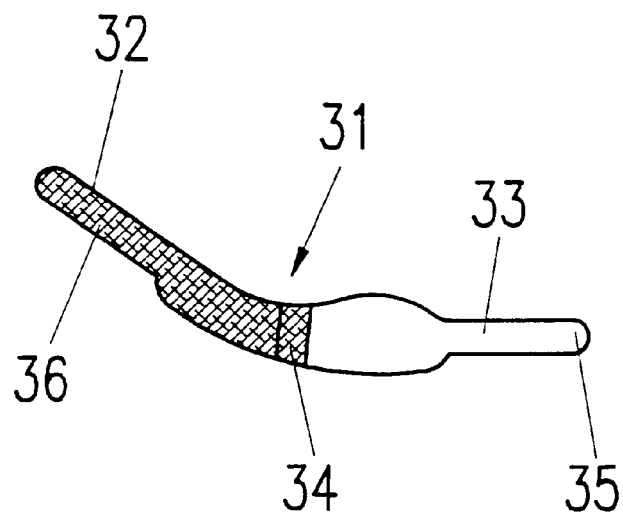
FIG. 3 shows a matrix manufactured according to the method.

In the punching device, the matrices shown in FIG. 3 are punched out of the composite foil, a matrix 31 consisting of a metal part 32 and a transparent synthetics part 33, the overlapping 34 being shown in a schematical manner. Both ends 35 and 36 of the matrix are narrower than the central portion in order to allow an easy insertion into the matrix tensioning device. The two different materials of the matrix need not be bonded together in the same manner as shown in FIG. 3 but it might be possible for other applications to combine the materials in lengthwise direction or according to still another arrangement.

The steel foil has in this example a thickness of 0.038 mm, but can have a thickness of about 0.020 to about 0.060 mm, still more preferably of about 0.03 to 0.04 mm. As a synthetic material foil, a polyester foil has been used, especially a polyethylene terephthalate foil known under the tradename "Mylar" having a thickness of about 0.04 to 0.08 mm as it is usual for dental matrices.

Using the steel foils and the polyester foils described above, and when the synthetics foil has been treated by a corona discharge, it became apparent that the UV curable adhesive manufactured by Dimax Corporation and sold under the tradename Dimax®128-M is a particularly advantageous product allowing to achieve a tensile strength that is considered as fully sufficient in the following clinical tests. Of course, this invention is not limited to this adhesive. Other light and UV curable adhesives having similar bonding properties and compatibilities such as Delo photobond, or a one-component, UV curable acrylate based adhesive may also be used.

What is claimed is:

1. A method for combining a metal foil with a synthetic material foil by adhesive bonding, comprising unwinding both foils from a supply roll each, subjecting the synthetic material foil to a corona discharge on at least a narrow border region of the foil, applying a light curing adhesive to at least one foil, pressing a portion of the metal foil to a portion of the synthetic foil to form a composite foil comprising a metal portion, an overlapping portion and a synthetic material portion, and irradiating the composite foil with light in order to cause polymerization of the adhesive.

2. The method of claim 1, wherein both foils are tensioned downstream the supply roll by a tension regulator in such a manner that the elongation of both materials is substantially the same, the metal foil being tensioned about 20 times the tensioning of the synthetic material foil.

3. The method of claim 1, wherein the metal foil and the synthetic material foil are offset to each other to such an extent that an overlapping width for cementing of about 2 to about 4 mm is obtained.

4. The method of claim 1, wherein the metal foil is a steel foil having a thickness of about 0.020 to about 0.060 mm.

5. The method of claim 1, wherein a polyester foil is used as the synthetic material foil, comprising a polyethylene terephthalate foil.

6. The method of claim 1, wherein the light curing adhesive is applied only to the edge portion of one surface of the metal foil.

7. The method of claim 6, wherein the corona discharge is applied to the narrow border region of the synthetic material foil.

8. The method of claim 7, wherein the edge portion of the metal foil is bonded to the narrow border region of the synthetic material foil.

9. The method of claim 2, wherein the tension regulator for the metal foil comprises a measuring gage, a lever and a pneumatically driven cylinder which acts on the lever to generate a tension in a deflector roller.

10. The method of claim 2, wherein the tension regulator for the synthetic material foil comprises a measuring gage, a lever and a mass which acts on the lever to generate a tension in a deflector roller.

11. A method for manufacturing a dental matrix by joining a metal foil with a synthetic material foil by adhesive bonding, comprising unwinding both foils from a supply roll each and subjecting the synthetic material foil, prior to the application of a light curing adhesive, to a corona discharge on at least a narrow border region of the foil, whereupon both foils are pressed together and irradiated by light, in order to cause polymerization of the adhesive, then transferring the composite foil thus obtained by a transportation device to a processing station for forming the matrix.

12. The method of claim 11, wherein the foils are tensioned downstream the supply roll by a tension regulator in such a manner that the elongation of both materials is substantially the same, the metal foil being tensioned about 20 times the tensioning of the synthetics foil.

13. The method of claim 11, wherein the metal foil and the synthetic material foil are offset to each other to such an extent that an overlapping width for cementing of about 2 to about 4 mm is obtained.

14. The method of claim 11, wherein the metal foil is a steel foil having a thickness of about 0.020 to about 0.060 mm.

15. The method of claim 11, wherein a polyester foil is used as the synthetic material foil, comprising a polyethylene terephthalate foil.

16. The method of claim 11, wherein the light curing adhesive is applied only to the edge portion of one surface of the metal foil.

17. The method of claim 16, wherein the corona discharge is applied to the narrow border region of the synthetic material foil.

18. The method of claim 17, wherein the edge portion of the metal foil is bonded to the narrow border region of the synthetic material foil.

19. The method of claim 11, wherein the matrix is formed by punching.

* * * * *